United States Patent [19]

Harvey

[11] Patent Number: 4,717,827
[45] Date of Patent: Jan. 5, 1988

[54] APPARATUS FOR ON-LINE SPECTROPHOTOMETRIC CHEMICAL ANALYSIS OF MATERIAL IN MOVING PROCESS STREAM

[75] Inventor: Robert J. Harvey, Charlotte, N.C.

[73] Assignee: Automatik Machinery Corporation, Charlotte, N.C.

[21] Appl. No.: 831,296

[22] Filed: Feb. 20, 1986

[51] Int. Cl.⁴ .......................................... G01N 21/00
[52] U.S. Cl. .................... 250/343; 356/246; 422/102
[58] Field of Search ................... 250/364, 428–432 R; 356/319, 326, 410, 411, 440, 246; 422/102; 436/171

[56] References Cited

U.S. PATENT DOCUMENTS

| | | | |
|---|---|---|---|
| 2,690,695 | 10/1954 | Coates | 356/246 |
| 2,885,863 | 5/1959 | Berger | 62/32 |
| 3,177,706 | 4/1965 | Shuman et al. | 356/440 X |
| 3,582,222 | 6/1971 | Hoblik | 356/246 |
| 3,614,243 | 10/1971 | Harvey | 356/246 |
| 3,646,313 | 2/1972 | Gorgone et al. | 219/200 |
| 3,886,364 | 5/1975 | Walker et al. | 250/343 |
| 4,529,306 | 7/1985 | Kilham et al. | 356/237 |

FOREIGN PATENT DOCUMENTS

| | | |
|---|---|---|
| 57-118348 | 1/1984 | Japan . |
| 667896 | 3/1952 | United Kingdom . |
| 1305214 | 1/1973 | United Kingdom . |

OTHER PUBLICATIONS

"Sampling Method Makes On-Stream IR Analysis Work", *Industrial Research and Development*, Sep., 1982, by Paul A. Wilks, Jr.
"Evolution of FTIR from the Laboratory to the Production Environment", *American Laboratory*, Dec., 1985, by F. Clark Hewitt, K. S. Morris and A. J. Rein.
"FTIR Analyzer for Real-Time, Multicomponent Analysis", *American Laboratory*, Dec., 1985, by Mark S. Roth and David O'Donnell-Leach.
"A Variable Path Length Infrared Cell for Use at Elevated Temperatures", LaTrobe University, 1973, by G. Butt, J. Chippindall, B, Ternai and R. D. Topsom.
"On-Line Monitoring System for Beverage Packaging Lines", *American Laboratory*, Dec. 1985, by Paul Wilks.

*Primary Examiner*—Barry S. Richman
*Assistant Examiner*—Michael S. Gzybowski
*Attorney, Agent, or Firm*—W. Thad Adams, III

[57] ABSTRACT

A spectrophotometric apparatus (10) utilizes a sample cell (14) to perform infrared spectrophotometric analysis on a moving process stream (11) containing, for example, polymer melt. Material to be analyzed flows between two closely spaced-apart crystals (40) in an observation chamber (42). Infrared radiation is transmitted from one side of the material through it to the other side. Crystals (40) are contained within threaded retainers (38) and (39) positioned in a bore. The retainers (38) and (39) can be moved towards and away from each other to vary the absorption rate of the material.

4 Claims, 10 Drawing Figures

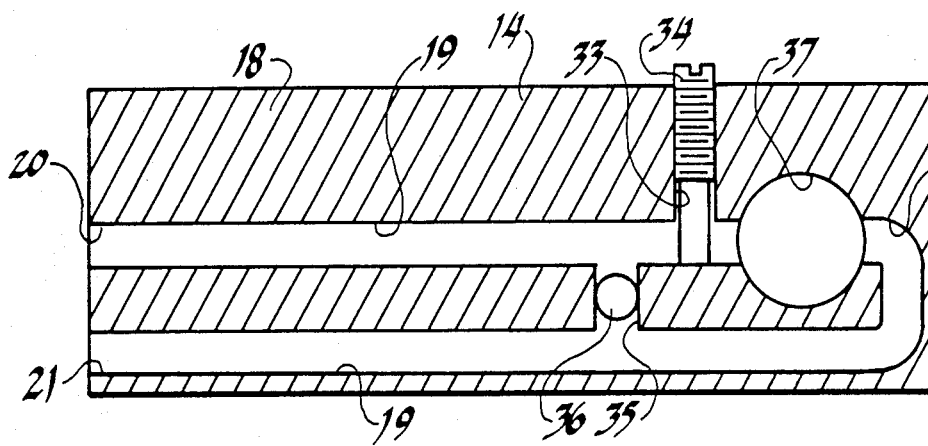
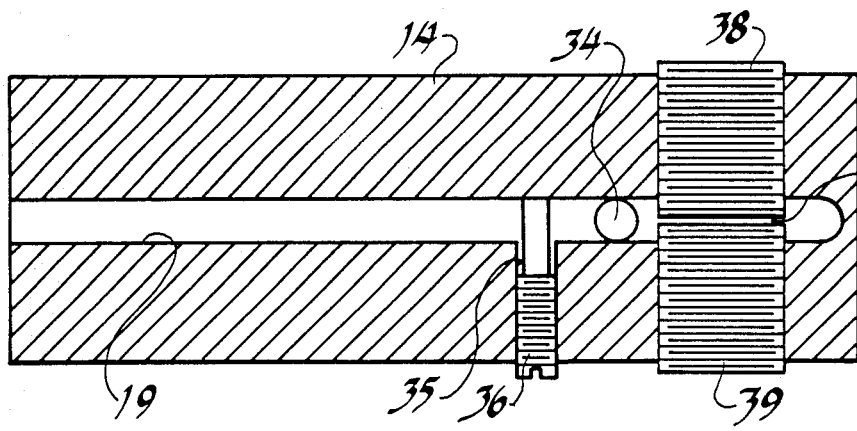

APPARATUS FOR ON-LINE SPECTROPHOTOMETRIC CHEMICAL ANALYSIS OF MATERIAL IN MOVING PROCESS STREAM

TECHNICAL FIELD AND BACKGROUND OF THE INVENTION

This invention relates to a method and apparatus for spectrophotometric chemical analysis of a material contained within a moving stationary process stream. The invention described in this application is intended specifically to be used on-line in a manufacturing or other process environment where rapid analysis of the chemical composition of a material in a moving process stream is critical to efficient and economical quality control. The invention disclosed in this application has a very wide range of use. For purposes of description and illustration, the spectrophotometric apparatus uses infrared form of radiation in order to obtain an infrared spectrum for analysis.

While chemical analysis of a wide range of materials is possible, the invention will be described for purposes of illustration with relation to the chemical analysis of a polymer melt contained and moving in a process stream such as in a polymer manufacturing facility or in a synthetic fiber manufacturing facility.

The infrared frequency range (2.5 to 50 microns or 4,800 to 200 wave numbers) has been used in infrared spectroscopy for some time. The popularity of infrared radiation as an analytical tool is the result of the relatively large amount of information that infrared spectroscopy provides and the manner in which it can be generated and analyzed. It is most widely used for the identification of all organic compounds and many non-organic compounds, and is useful because it can analyze a sample whether in the solid, liquid molten or gas phase and whether the materials are pure or impure. Depending on the manner of use, both qualitative and quantitative information can be provided. Analysis of infrared radiation output data is relatively rapid, lending itself to at least theoretical use in on-line processes. However, the physical problems associated with testing of materials in an on-line environment have been difficult. Accordingly, most infrared analysis has been and still is conducted in a laboratory environment. In the polymer manufacturing and processing environment described above, the typical method of qualitative analysis of the polymer melt is to take a sample from the end product, i.e., flake or pellet and deliver it to a laboratory location for infrared analysis. This procedure is particularly unsuitable because of the nature of the polymer manufacturing process. Polymers, such as polypropylene, polyethylene, nylon and the like are produced from the reaction of various organic compounds at very high temperatures and pressures on the order of approximately 572° F. (300° C.) and 2500 psi (1,757,750 kg/m$^2$). Maintenance of this temperature and pressure throughout the process stream is essential, since the polymer very quickly hardens into a virtually indestructible mass upon cooling. For this reason, polymer manufacturing facilities typically run twenty-four hours a day, seven days a week for several months. Therefore, a polymer manufacturing plant of relatively modest size will manufacture polymer in hugh quantities. The many different uses for polymers require that they be manufactured according to many varying formulas. A typical polymer will contain several primary constituent parts and many secondary additives, often in minute quantities, which nevertheless have a significant affect on the qualities of the end product. For example, in polymers such as polyester and nylon, additives to the polymer mix reduce the coefficient of friction of yarn manufactured from the polymer so that yarn guides, rings and the like which come into contact with the rapidly moving yarn do not wear out rapidly. Other additives and formulation end groups in the polymer control the rate and extent to which the polymer absorbs and reacts with dyes. Still other additives affect the strength, elongation, moisture absorption rate and many other characteristics. Infrared analysis of polymer is typically carried out by forming a film or melt from polymer flake or pellets. The film or melt is allowed to cool and, when analyzed in the laboratory, is analyzed in its cool state. Infrared analysis of polymer at ambient temperature gives results which may differ considerably from analysis of the same polymer at its process stream temperature. This limits the utility of the information obtained. Even if the polymer melt is reheated, the results will still not provide a completely accurate reflection of the polymer melt in the process stream since, each time the polymer melt is heated, cooled and reheated, its chemical composition changes somewhat due to heat related reaction of the polymer components and the escape of volatiles from the polymer caused by heating. Even if reasonably accurate results are achieved, the length of time which necessarily elapses between the taking of the sample, the completion of the infrared analysis in the laboratory and the correction of the formula can result in the manufacture of vast quantities of polymer which exceed quality control limitations and must be reprocessed, thrown away or sold as waste or second quality product.

Therefore, it is highly desirable to sample and carry out infrared radiation analysis of materials such as polymers on an on-line basis at the process stream. On-line infrared analysis of some materials is known. For example, infrared analysis of water to determine its sugar and/or carbon dioxide content is carried out using the principle of circular internal reflection. A cylindrical crystal of an infrared transmissive material is sealed into a chamber through which flows a sample stream from the beverage line. Infrared radiation is focused on one end of the cylinder and reflected internally through it to the other end where, as it exits, it is split into three sections by selected filtration of the infrared spectrum. One of the sections passes radiation at the sugar absorption band, the second at the carbon dioxide absorption band and the third provides a reference wavelength. In this usage, the cylinder is referred to as a probe and the radiation samples the liquid which passes across the outer surface of the probe.

While this system has limited utility in the analysis of relatively fluid, non-viscous liquids such as water and beverage mix, the use of a probe cannot be presently used to conduct infrared analysis of relatively opaque, viscous substances such as polymer melt. This is for a variety of reasons. First, the crystal is difficult to heat uniformly to the temperature of the process stream. In the case of the relatively high temperatures necessary to maintain a polymer melt at its process stream temperature, even momentary contact by the polymer stream with a relatively cooler object such as the probe will cause a relatively thick film or coating of polymer to form and cling to the probe. Thereafter, the infrared radiation is only sampling the stationary material clinging to the probe to a depth of 4 to 8 microns and not the material in the moving process stream.

The development of a sample cell which permits on-line chemical analysis of polymer melt in a moving process stream permits samples to be taken and quality variations detected with sufficient speed so that corrections can be made before significant amounts of waste or second quality polymers are produced. Furthermore, the development of such a sample cell permits the continuous sampling of the polymer melt. Such a continuous process permits the establishment of alarm limits which automatically alerts production personnel when the chemical composition of the polymer melt varies outside of specifications, diverts defective polymer melt out of the process stream for reprocessing or even, through suitable servo-mechanisms, controls upstream processes to bring the chemical analysis back within standards.

The present invention solves this problem by, in effect, taking a moving "slice" of a material, such as polymer melt and, while maintaining it at its precise process stream temperature and pressure, passing infrared radiation through it from one side to the other.

SUMMARY OF THE INVENTION

Therefore, it is an object of the invention to provide a sample cell for chemical analysis of a material in a moving process stream by spectrophotometric means.

It is another object of the invention to provide a sample cell which permits a material in a moving process stream to be chemically analyzed by passing radiation through the material from one side of the material to the other and in a noninvasive manner.

It is another object of the invention to provide a sample cell which permits the material to be maintained at its process stream temperature and pressure during radiation analysis.

It is another object of the invention to provide a sample cell which permits the material to be either discarded or introduced back into the moving process stream after analysis.

It is yet another object of the present invention to provide a sample cell which permits infrared radiation chemical analysis of a moving process stream of polymer melt at its process stream temperature and pressure.

It is another object of the invention to provide a method for chemically analyzing a material in a moving process stream by full scan (2.5 to 50 microns) spectrophotometric means to accomplish the objects set forth above.

BRIEF DESCRIPTION OF THE DRAWINGS

Some of the objects of the invention have been set forth above. Other objects and advantages of the invention will appear as the description of the invention proceeds when taken in conjunction with the following drawings, in which:

FIG. 9 is a vertical cross-section, with parts omitted for clarity, showing the valving arrangement and observation chamber of the sample cell; and FIG. 10 is a horizontal cross-section of the sample cell shown in FIG. 9, with parts omitted for clarity, showing the valving arrangement and the observation chamber of the invention.

DESCRIPTION OF THE PREFERRED EMBODIMENT

Figure 1:
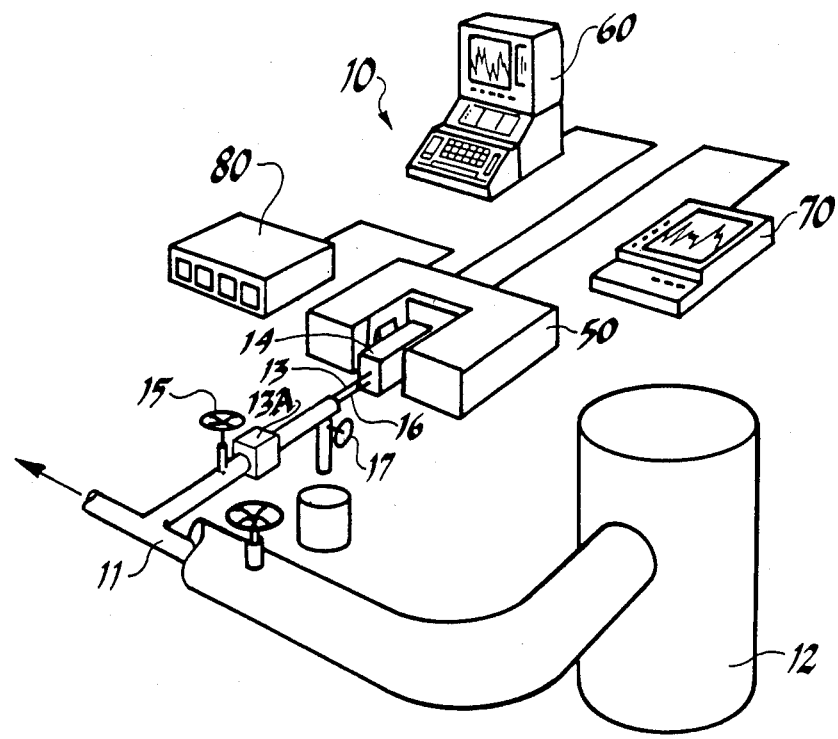
FIG. 1 is a schematic view of the spectrophotoscopic apparatus which includes the invention according to the application, in communication with a process stream.

Referring now specifically to the drawings, a spectrophotometric apparatus according to the present invention is broadly illustrated and designated by reference numeral 10. Apparatus 10 samples a material moving in a process stream 11. For the purposes of description of the invention, the material in the process stream is considered to be polymer melt which is flowing downstream of a source such as a reaction vessel 12 where the polymer is created. Of course, in other environments the upstream source may be a heated vessel where polymer in chip, pellet or flake form manufactured elsewhere is reheated to its melted state for further processing. Polymer melt is diverted from the process stream 11 through a feeder line 13 which is contained within an insulated jacket 13A to maintain the polymer melt at its process stream temperature. Flow to feeder line 13 may be controlled by a feed pump 13B and a gate valve 15. Polymer melt flows from feeder line 13 into a sample cell 14 according to the present invention. The sample is analyzed by infrared radiation by means of a spectrometer 50. The analysis process is controlled by a compute 60 which also displays the infrared spectra generated by the analysis of the polymer melt. The analysis shown on the display terminal of the computer 60 can be obtained in hard copy form from a plotter 70. The temperature of the polymer melt within sample cell 14 is controlled by a temperature regulator 80, as will be described in further detail below.

Figures 2, 3:
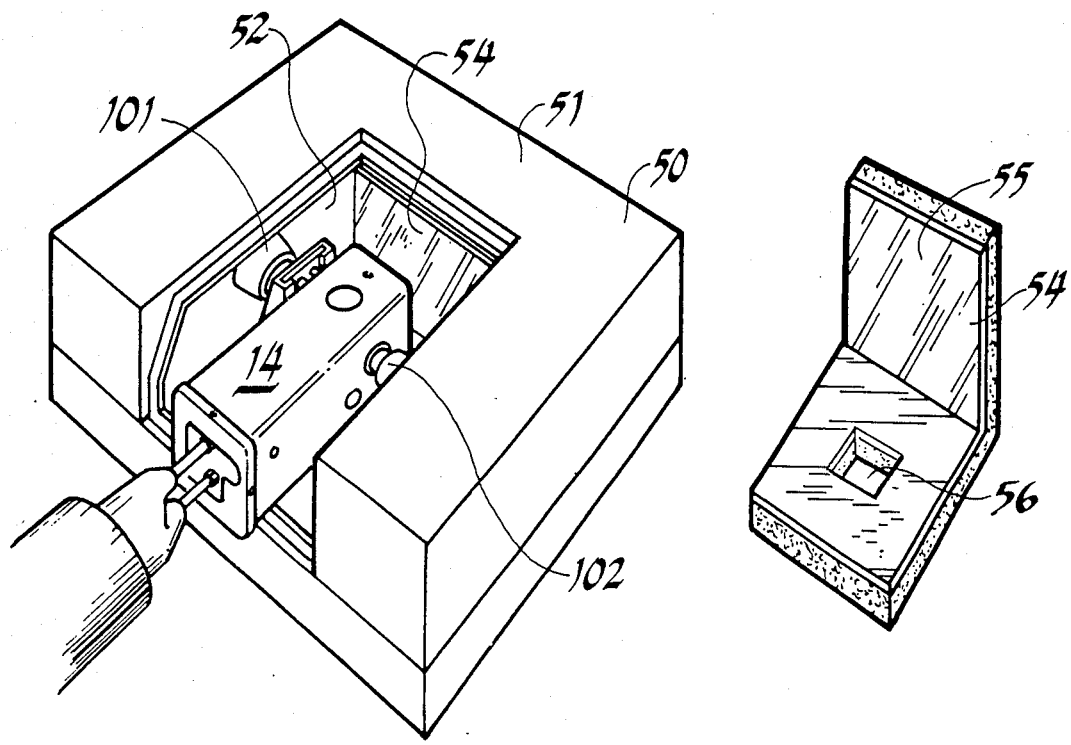
FIG. 2 is a perspective view of the spectrometer and sample cell shown in FIG. 1.
FIG. 3 is a perspective view of a heat insulative and reflective barrier which protects the spectrometer from heat given off by the sample cell.

Referring now to FIG. 2, the spectrometer 50 is contained within a housing 51 which includes a bay 52 within which sample cell 14 is positioned.

Figure 4:
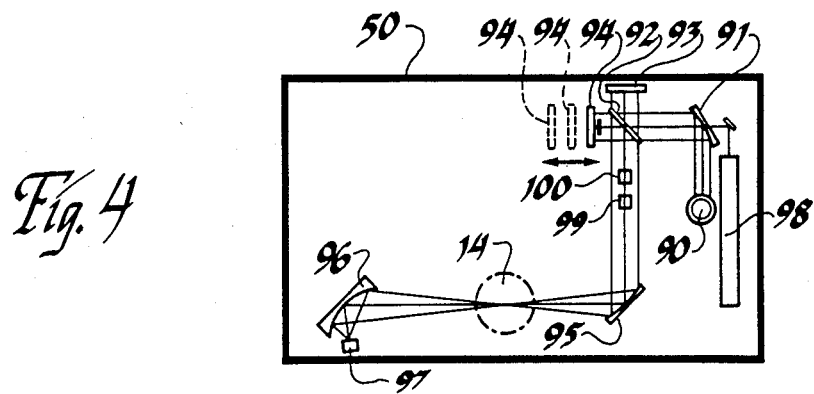
FIG. 4 is a schematic of a Fourier Transform infrared spectrometer with a Michelson interferometer used in connection with the sample cell according to this invention.

Spectrometer 50 is illustrated in further detail in FIG. 4. An infrared radiation source 90 is reflected at right angles off a mirror 91 and through a beam splitter 92. Fifty percent of the infrared light is reflected to a fixed mirror 93 and 50 percent of the light is transmitted to a moving mirror 94. The fixed mirror 93 returns the infrared radiation by reflection back to the beam splitter along a fixed optical path. The moving mirror 94 reflects radiation back at pathlengths that are variable and thus may differ from the fixed mirror. The reflected beams then recombine at the beam splitter 92 and a portion of this recombined beam is directed to a focusing lens 95. Lens 95 directs the converging infrared beam to a focus point within sample cell 14 where the infrared beam again diverges. The beam is reflected again by a focusing lens 96 to an infrared detector 97. A laser 98 is used to measure the change in optical path difference within spectrometer 50. The laser 98 emits a beam with a very precise interference pattern which yields an interferogram which is a cosine wave. This cosine wave triggers the digitization of the detector signal. Spectrometer 50 also includes a laser detector 99 and a white light detector 100.

Spectrometer 50 is very susceptible to heat. Since, as described below, the polymer melt must be maintained at its process stream temperature, an L-shaped insulated barrier 54 is positioned within bay 52 and prevents heat from sample cell 14 from damaging inferometer 50. As is best shown in FIG. 3, barrier 54 comprises a right angle structure of insulative material 54, such as a product known as Microfelt onto which is bonded a highly polished, reflective aluminum or chrome steel sheet 55. Sample cell 14 is mounted in bay 52 through access port 56.

Figure 5:
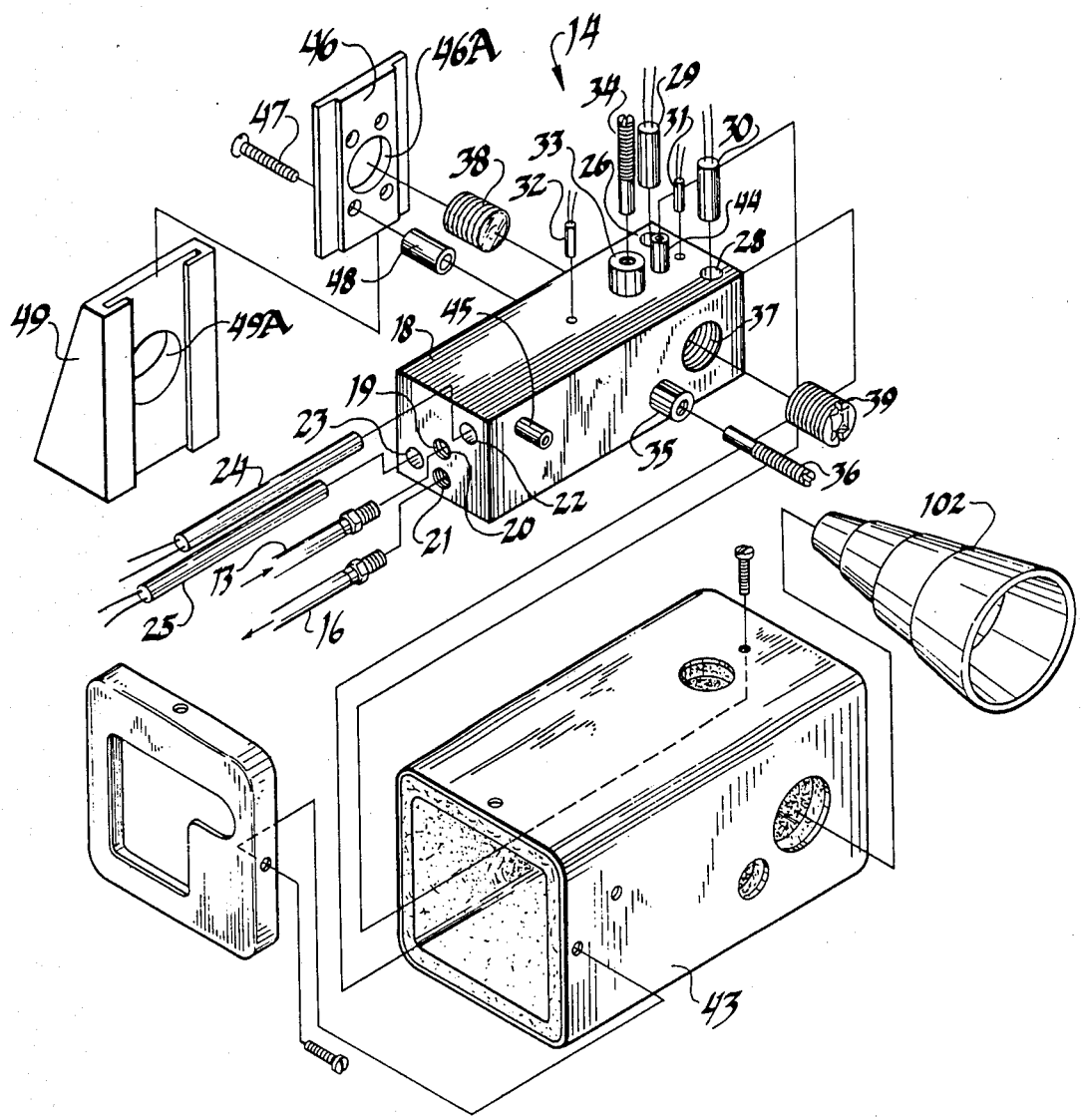
FIG. 5 is an exploded perspective view of a sample cell according to an embodiment of the invention.

Referring now to FIG. 5, sample cell 14 is described in detail. The core of sample cell 14 is a steel block 18 into which is formed a conduit 19. Conduit 19 is substantially U-shaped and begins at a threaded inlet 20 which connects with feeder line 13 and ends at an outlet 21 directly beneath inlet 20 which discharges polymer melt into a discharge line 16.

Two longitudinally extending bores 22 and 23 are formed in block 18 and receive elongate resistance-type heaters 24 and 25. Heaters 24 and 25 parallel conduit 19 in relatively close relation and are intended to maintain the polymer within block 18 at its process stream temperature. Two additional bores 26 and 28 contain elongate resistance heaters 29 and 30, which maintain the polymer melt at its process stream temperature in the area of the observation chamber, as described below. A thermocouple 31 monitors the temperature in the vicinity of heaters 29 and 30. A like thermocouple 32 monitors the temperature of the block 18 in the area of heaters 24 and 25. Heaters 24, 25, 26 and 28, and thermocouples 31 and 32 are controlled and monitored by regulator 80.

A threaded temperature sample valve access port 33 is formed in block 18 and communicates with conduit 19. A plug valve 34 having mating threads thereon is positioned in sample valve access port 33 and is movable between positions wherein polymer melt is permitted to flow into the observation zone and a closed position at which flow to the observation zone is not permitted. A bypass valve access port 35 is formed in block 18 and also communicates with conduit 19. A bypass plug valve 36 with mating threads thereon is positioned in bypass access port 35 and is movable between open and closed positions. The function of these valves is further explained with reference to FIGS. 9 and 10, below. A threaded retainer bore 37 is formed in and extends through block 18 from one side to the other. A threaded retainer 38 is positioned in bore 37 from one side and a like threaded retainer 39 is positioned in bore 37 from the other side.

Figures 6, 7:
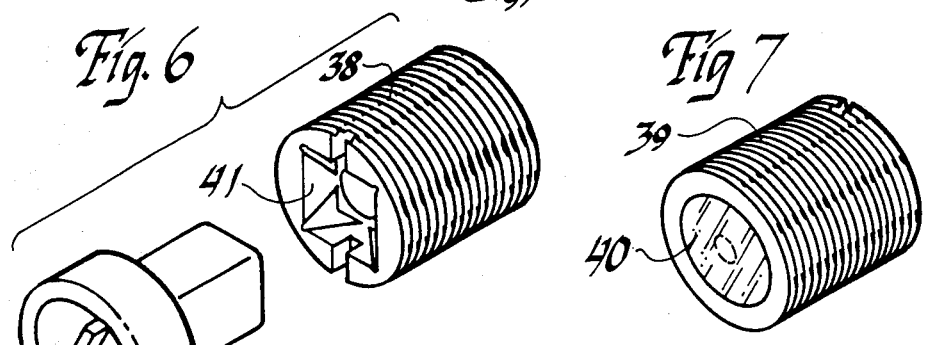
FIG. 6 is a perspective view of one embodiment of a window retainer according to the present invention.
FIG. 7 is a perspective view from the end opposite that shown in FIG. 6 of a window retainer in accordance with the invention.
Figure 8:
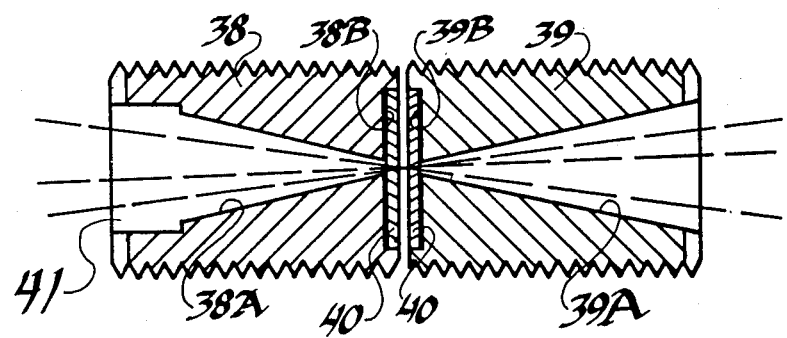
FIG. 8 is a cross-section of the retainers shown in FIGS. 6 and 7.

Referring now to FIGS. 6, 7 and 8, the structure of retainers 38 and 39 will be explained. As is best shown in FIG. 8, retainers 38 and 39 have tapered apertures 38A and 39A, respectively, extending through them from one end to the other. An annular shoulder recess 38B is formed in one end of recess 38 and an annular recess 39B is formed in one end of retainer 39. Disk-shaped crystals 40 of an infrared transmissible substance such as zinc selenide (ZnSe) are fixedly secured into recesses 38B and 39B by a high temperature adhesive such as epoxy cement. The crystals 40 form "windows" through which infrared radiation is directed. Note that crystals 40, which for example are 0.72 in. (18 mm) in diameter and 0.16 in. (4 mm) thick are supported on virtually their entire surface area by retainers 38 and 39, respectively, with only a central exposed aperture of 0.32 in. (8 mm) diameter allowing for the transmission of radiation. This permits crystals 40 to withstand very high temperature and pressure.

As shown in FIG. 6, retainer 38 includes in its end opposite crystal 40 a square cutout 41 adapted to receive the socket of a socket wrench. This is but one of many means by which either one or the other or both of retainers 38 and 39 can be adjusted relative to each other.

As is shown in FIGS. 9 and 10, bore 37 intersects conduit 19 downstream of sample valve access port 33. Retainers 38 and 39 are positioned in bore 37 in closely spaced-apart relation. The space between crystals 40 in retainers 38 and 39 define an observation chamber 42. As polymer melt flows from conduit 19 into and through observation chamber 42, it is exposed to the transmission of infrared radiation through it from side to the other.

With sample valve 34 in the open position, the polymer melt flows between crystals 40 of retainers 38 and 39, forming an extremely thin sample of polymer through which infrared radiation is transmitted from one side of the sample to the other. The polymer melt continues downstream in conduit 19 and exits through discharge outlet 21 into discharge line 16. Discharge line 16 can be valved with a valve 17 so that the polymer melt may be discarded or reintroduced back into the process stream 11, as desired.

If sampling is not carried on continuously, sample valve 34 is closed and bypass valve 36 is opened at predetermined intervals. In this configuration, the polymer melt is blocked from entering observation chamber 42 and instead passes through bypass valve access port 35 into conduit 19 upstream of observation chamber 42 and out through discharge outlet 21, as described above.

There is a third possibility for routing polymer melt through block 18. This involves having sample valve 34 and bypass valve 36 both open to a predetermined extent. This would most usually be done when continuous sampling is desired. In this procedure, sample valve 34 is opened sufficiently so that, for example, approximately 10 percent of the polymer melt in conduit 19 flows past sample valve 34 and into observation chamber 42. Bypass valve 36 is opened to a considerably greater extent so that the remaining 90 percent of the polymer melt bypasses observation chamber 42 and exits through discharge outlet 21. By regulating sample valve 34 and bypass valve 36 relative to each other, the percentage of the polymer melt in conduit 19 which is sampled and analyzed in observation chamber 42 can be varied to obtain a more rapid sample.

Referring again to FIG. 5, the remaining components of sample cell 14 will be briefly described. Block 18 is contained within an insulated cover 43. Suitable apertures are formed in cover 43 to permit access to block 18. Block 18 is supported within cover 43 by the insulation and also by a pair of stand-offs 44 and 45 which attach to the cover 43 by screws. Block 18 and cover 43 are secured within bay 52 of spectrometer 50 by means of a male mounting plate 46 which is secured through cover 43 to block 18 by screws 47 and stand-offs 48, one of each of which is shown in FIG. 5. Holder 46 mates with a female holder 49 mounted in bay 52 of spectrometer 50. Holders 46 and 49 include apertures 46A and 49A, respectively, through which the infrared beam is passed. Two cone-shaped axially adjustable tubes 101 and 102 mate with retainers 38 and 39 and therefore fully enclose the infrared beam as it passes through sample cell 14. Ordinarily, tubes 101 and 102 are purged to prevent interference from water vapor and carbon dioxide with the infrared radiation.

Referring again to FIG. 8, retainers 38 and 39 are adjusted so that infrared beam defines a focus point in observation chamber 42. By adjusting the distance between retainers 38 and 39 slightly, the degree of absorption desired to obtain the most accurate results can be achieved. It is anticipated that retainers 38 and 39 will eventually be controlled by calibrated means so that a predetermined space between retainers 38 and 39 will correlate with a desired absorption rate of a particular material being tested. Otherwise, the optimum width of observation chamber 42 is determined empirically by moving the two crystals 40 into contact with each other and then backing one or both of the retainers 38 and 39 out of bore 37 and observing the effect on the absorption rate of the material achieved by increasing the pathlength accordingly. Insofar as in known, the maximum effective pathlength for sampling polymer melt is no more than about 30,000ths of an inch (0.76 mm).

The use of the sample cell 14 above permits accurate spectrophotometric analysis of a material within a process stream. In addition to the use of infrared radiation, radiation in the visible, ultraviolet and other spectra can be used. One major advantage of the sample cell 14 is that the sample is taken and analyzed in a noninvasive manner, as distinguished from the invasive probe known in the prior art.

Consistent with the significant temperatures and pressures to which sample 14 may be exposed, its primary components are constructed of high-grade stainless steel. All of the conduits are polished, as are the machine threads. In addition, the threads can be wrapped with Teflon tape. No brass, copper or other material which might react with the material being analyzed is used.

Finally, a pressure transducer, not shown in the drawings, may be provided to monitor pressure within conduit 19.

A sample cell for the chemical analysis of a material in a moving process stream by spectrophotometric means is described above. Various details of the invention may be changed without departing from its scope. Furthermore, the foregoing description of a preferred embodiment of a sample cell according to the present invention is provided for the purpose of illustration only and not for the purpose of limitation - the invention being defined by the claims.

I claim:

1. A sample cell for chemical analysis of material in a moving process stream by spectrophotometric means, said sample cell comprising:
   (a) a housing;
   (b) a through bore formed in said housing;
   (c) a first radiation transmissible window movably positioned in said bore;
   (d) a second radiation transmissible window movably positioned in said bore in opposed, variable, spaced-apart relation to said first radiation transmissible window and defining therebetween an observation chamber having a path length which is varied by movement of said first and second windows relative to each other;
   (e) an inlet conduit formed in said housing and communicating for fluid flow with said observation chamber for admitting material in a process stream into the observation chamber;
   (f) an outlet conduit in said housing and communicating for fluid flow with said observation chamber for discharging material from the observation chamber;
   (g) said inlet conduit and said outlet conduit being axially aligned in a common vertical plane on an upstream and a downstream side of the observation chamber, respectively, to permit an axially direct flow of material into and out of the observation chamber; and
   (h) said first and second windows being variably adjustable by symmetrical movement with respect to each other and to the inlet conduit and outlet conduit to define the observation chamber as having an adjustable pathlength relative to the inlet conduit and outlet conduit whereby material may flow directly through the inlet conduit into said observation chamber, past said first and second windows and out of said observation chamber through the outlet conduit thereby minimizing turbulence and shear in the material.

2. A sample cell according to claim 1, and including valve means cooperating with said inlet conduit for selectably
   (a) directing material into and through said observation chamber, or
   (b) directing material into the outlet conduit without first passing through said observation chamber.

3. A sample cell according to claim 1, and including valve means cooperating with said inlet conduit for selectably
   (a) directing material into and through said observation chamber, or
   (b) directing material into the outlet conduit without first passing through said observation chamber, or
   (c) simultaneously directing a first predetermined portion of material through said observation chamber and a second predetermined portion of material into the outlet conduit without first passing through said observation chamber.

4. A sample cell according to claim 1, wherein said first and second radiation transmissible windows comprise an infrared transmissible material.

* * * * *